US010322811B2

(12) United States Patent
Breigenzer et al.

(10) Patent No.: US 10,322,811 B2
(45) Date of Patent: Jun. 18, 2019

(54) AIR PURIFICATION SYSTEM AND METHOD OF ASSEMBLING

(71) Applicant: The Boeing Company, Chicago, IL (US)

(72) Inventors: Thomas James Breigenzer, Everett, WA (US); Fue Chue Vue, Mill Creek, WA (US)

(73) Assignee: The Boeing Company, Chicago, IL (US)

( * ) Notice: Subject to any disclaimer, the term of this patent is extended or adjusted under 35 U.S.C. 154(b) by 71 days.

(21) Appl. No.: 15/168,374

(22) Filed: May 31, 2016

(65) Prior Publication Data

US 2017/0341762 A1    Nov. 30, 2017

(51) Int. Cl.
*B64D 13/06*   (2006.01)
*A61L 9/20*   (2006.01)
(Continued)

(52) U.S. Cl.
CPC ............ *B64D 13/06* (2013.01); *A61L 9/20* (2013.01); *B01D 46/0001* (2013.01); *B01D 46/0013* (2013.01); *B01D 46/0023* (2013.01); *B01D 46/0024* (2013.01); *B01D 46/0027* (2013.01); *B01D 46/0028* (2013.01); *B01D 46/0036* (2013.01); *B01D 46/12* (2013.01);
(Continued)

(58) Field of Classification Search
CPC ............. B64D 13/06; B64D 13/08; B64D 2013/0603–0696; B01D 46/0001; B01D 46/0002; B01D 46/0013; B01D 46/0023; B01D 46/0024; B01D 46/0027; B01D 46/0028; B01D 46/0036; B01D 46/12; B01D 53/0415; B01D 53/0438; B01D 2259/4575; B01D 2265/02; B01D 2267/40; B01D 2279/40
See application file for complete search history.

(56) References Cited

U.S. PATENT DOCUMENTS

| 5,853,445 A | 12/1998 | Wong et al. |
| 7,384,456 B2 * | 6/2008 | Aubert ................. B03C 3/12 422/186.04 |

(Continued)

FOREIGN PATENT DOCUMENTS

| DE | 202004017858 U1 | 3/2005 |
| EP | 0839538 A2 | 5/1998 |

OTHER PUBLICATIONS

Flanders Corporation, Washington, NC; "PF-1 Pureframe Filter Holding Frames and Fasteners"; Bulletin PB1308-0211; available at http://www.flanderscorp.com/files/FlandersFFI_literature/PB1308. pdf; last visited May 31, 2016.

(Continued)

*Primary Examiner* — Timothy C Cleveland
(74) *Attorney, Agent, or Firm* — Armstrong Teasdale LLP

(57) ABSTRACT

A filter assembly including a plurality of filter modules, wherein each filter module in the plurality of filter modules includes a frame, a filtration element coupled within the frame, and at least one mating feature. The at least one mating feature of each filter module is configured for selective engagement with the at least one mating feature of another filter module such that the plurality of filter modules are coupled together in a serial arrangement.

19 Claims, 4 Drawing Sheets

(51) Int. Cl.
  B01D 46/00  (2006.01)
  B01D 53/04  (2006.01)
  B01D 46/12  (2006.01)

(52) U.S. Cl.
  CPC ..... *B01D 53/0415* (2013.01); *B01D 53/0438* (2013.01); *B01D 2259/4575* (2013.01); *B01D 2265/02* (2013.01); *B01D 2267/40* (2013.01); *B01D 2279/40* (2013.01); *B64D 2013/0651* (2013.01); *B64D 2013/0685* (2013.01); *B64D 2013/0688* (2013.01)

(56) References Cited

U.S. PATENT DOCUMENTS

| | | |
|---|---|---|
| 2006/0162300 A1 | 7/2006 | Sharifi |
| 2015/0273378 A1 | 10/2015 | Sohn et al. |
| 2017/0056812 A1* | 3/2017 | Meirav ............. B01D 53/0415 |

OTHER PUBLICATIONS

Air Filters, Inc., Houston, TX; "Filter Housings for Every Application"; available at http://www.airfilterusa.com/filter-housing?_vsrefdom=ppcgoogle&kw=%2Bair%20%2Bfilter%20%2Bhousing&nw=g&dev=c&ex=f06hqo-eep549-mci8ik&gclid=CKTmx6DAhM0CFQepaQodsfcPXw; last visited May 31, 2016.
EPO Extended Search Report for related application 17155509.7 dated Sep. 20, 2017; 7 pp.

* cited by examiner

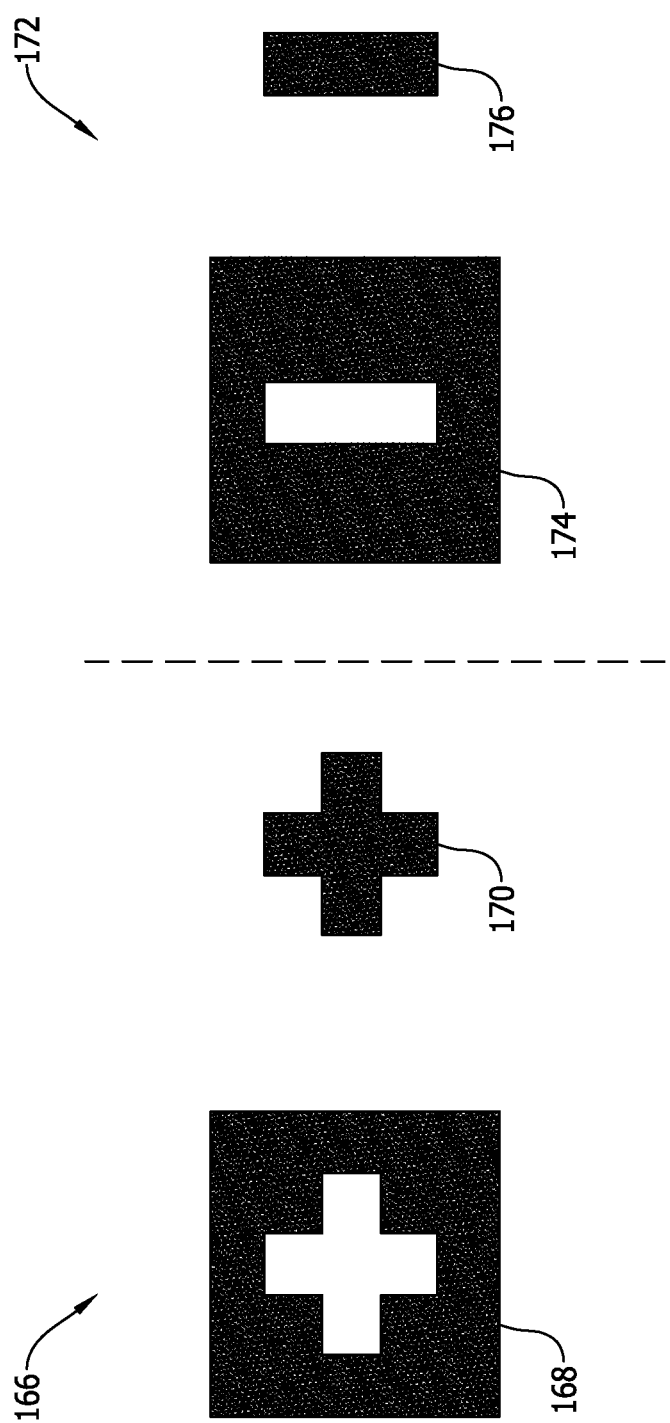

AIR PURIFICATION SYSTEM AND METHOD OF ASSEMBLING

BACKGROUND

The field of the present disclosure relates generally to filtration systems and, more specifically, to an air purification system including a plurality of filter modules coupled together in series.

At least some known air distribution systems use filters to capture contaminants, such as bacteria and viruses, before recirculating the air into a room, a compartment, or a passenger cabin of a vehicle, for example. More specifically, in an air distribution system for use on an aircraft, the type and capabilities of the filters are typically selected based on aircraft model and typical mission profile, and the filters are then packaged as a single unitary unit. However, system performance and filtration options for an air distribution system can be limited by predefined filter packages, and changing the performance or filtration capabilities of the filter packages may require the use of a custom aftermarket solution.

BRIEF DESCRIPTION

In one aspect, a filter assembly is provided. The filter assembly includes a plurality of filter modules, wherein each filter module in the plurality of filter modules includes a frame, a filtration element coupled within the frame, and at least one mating feature. The at least one mating feature of each filter module is configured for selective engagement with the at least one mating feature of another filter module such that the plurality of filter modules are coupled together in a serial arrangement.

In another aspect, an air purification system is provided. The system includes an inlet, an outlet, and a filter assembly including plurality of filter modules positioned between the inlet and the outlet. Each filter module in the plurality of filter modules includes a frame, a filtration element coupled within the frame, and at least one mating feature. The at least one mating feature of each filter module is configured for selective engagement with the at least one mating feature of another filter module such that the plurality of filter modules are coupled together in a serial arrangement.

In yet another aspect, a method of assembling an air purification system having an inlet and an outlet is provided. The method includes positioning a filter assembly between the inlet and the outlet, wherein the filter assembly includes a plurality of filter modules. The method also includes selectively engaging the plurality of filter modules with each other such that the plurality of filter modules are coupled together in a serial arrangement. Each filter module includes at least one mating feature for coupling the plurality of filter modules together, and the at least one mating feature of each filter module is selected such that the serial arrangement is predetermined.

BRIEF DESCRIPTION OF THE DRAWINGS

FIG. 4 is a schematic illustration of exemplary mating features that may be used with the filter modules shown in FIG. 2.

DETAILED DESCRIPTION

The implementations described herein relate to an air purification system including a filter assembly that includes a plurality of filter modules coupled together in series. More specifically, the air purification system includes an inlet, an outlet, and a plurality of filter modules positioned between the inlet and the outlet. Each filter module includes a frame, a filtration element, and at least one mating feature. The at least one mating feature of each filter module enables the plurality of filter modules to be coupled together in a serial arrangement. Moreover, the filter modules can include different filtration elements, such as a particulate filter media, an absorptive filter media, and functional filtration devices. As such, the filter modules are selectively and individually interchangeable, which enables the air purification system to be tailored with specific filtration capabilities, and facilitates increasing the service life of the filter assembly.

As used herein, an element or step recited in the singular and proceeded with the word "a" or "an" should be understood as not excluding plural elements or steps, unless such exclusion is explicitly recited. Furthermore, references to "exemplary implementation" or "one implementation" of the present disclosure are not intended to be interpreted as excluding the existence of additional implementations that also incorporate the recited features.

Figure 1:
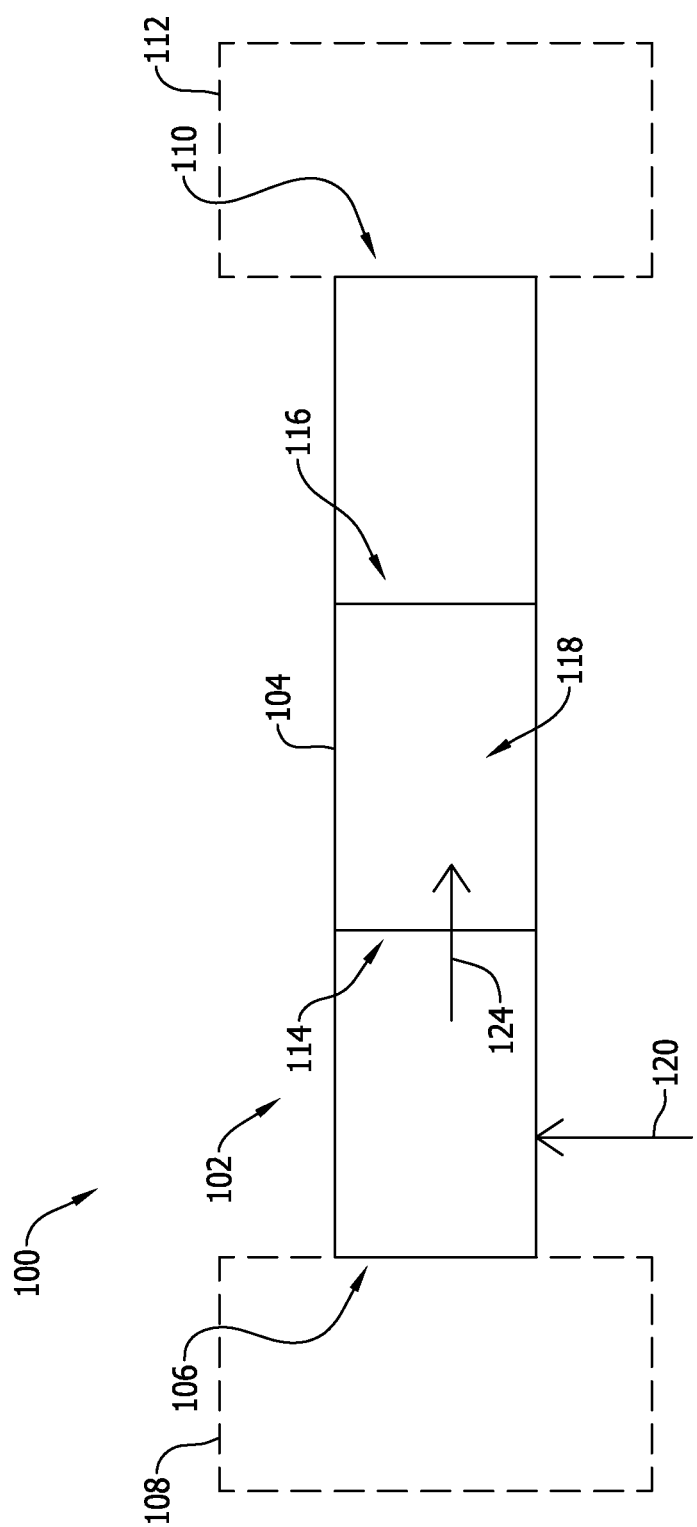
FIG. 1 is a schematic illustration of an exemplary air distribution system.

FIG. 1 is a schematic illustration of an exemplary air distribution system 100. In the exemplary implementation, air distribution system 100 includes a duct 102 and an air purification system 104 positioned within duct 102. Duct 102 includes a duct inlet 106 for receiving airflow from a source 108, and a duct outlet 110 for discharging airflow to a predetermined location 112 (e.g., a room, a passenger cabin, or a compartment). Air purification system 104 includes an inlet 114, an outlet 116, and a filter assembly 118 positioned between inlet 114 and outlet 116, as will be described in more detail below. Air purification system 104 is located between duct inlet 106 and duct outlet 110. More specifically, airflow is channeled through filter assembly 118 before being channeled towards duct outlet 110 to facilitate removing contaminants from the air channeled through duct 102 from source 108. For example, the contaminants may be in either solid particulate, such as dust, pollen, mold, bacteria, and viruses, or gaseous form.

In a particular implementation, air distribution system 100 is included onboard an aircraft (not shown), for example, as part of an environmental control system (ECS) of the aircraft. In such an implementation, duct 102 is a recirculation duct and source 108 and location 112 are both a passenger cabin, are both a cockpit, are both a crew compartment, or are both a cargo compartment, for example. When recirculating the air, a secondary air stream 120 (e.g., an ambient air stream) is optionally injected upstream from air purification system 104 such that the secondary air is mixed with the airflow from source 108. For example, secondary air stream 120 is injected into source 108 and/or duct 102 upstream from air purification system 104. Injecting secondary air stream 120 upstream from air purification system 104 facilitates removal of particulates or contaminants from the ambient environment, for example, before discharging filtered air towards duct outlet 110. Alternatively, air distribution system 100 receives airflow from a source 108 that is different than location 112 receiving the filtered air. For example, air distribution system 100 can channel airflow from one compartment within the aircraft as source 108 to a different compartment within the aircraft as location 112. Moreover, while air distribution system 100 is capable of use within an aircraft, air distribution system 100 can also be implemented in any structure through which air flows, such as a building, a platform, or a vehicle. Further, air purification system 104 is capable of utilization in any system where filtering contaminants from a stream of air is desired.

Figure 2:
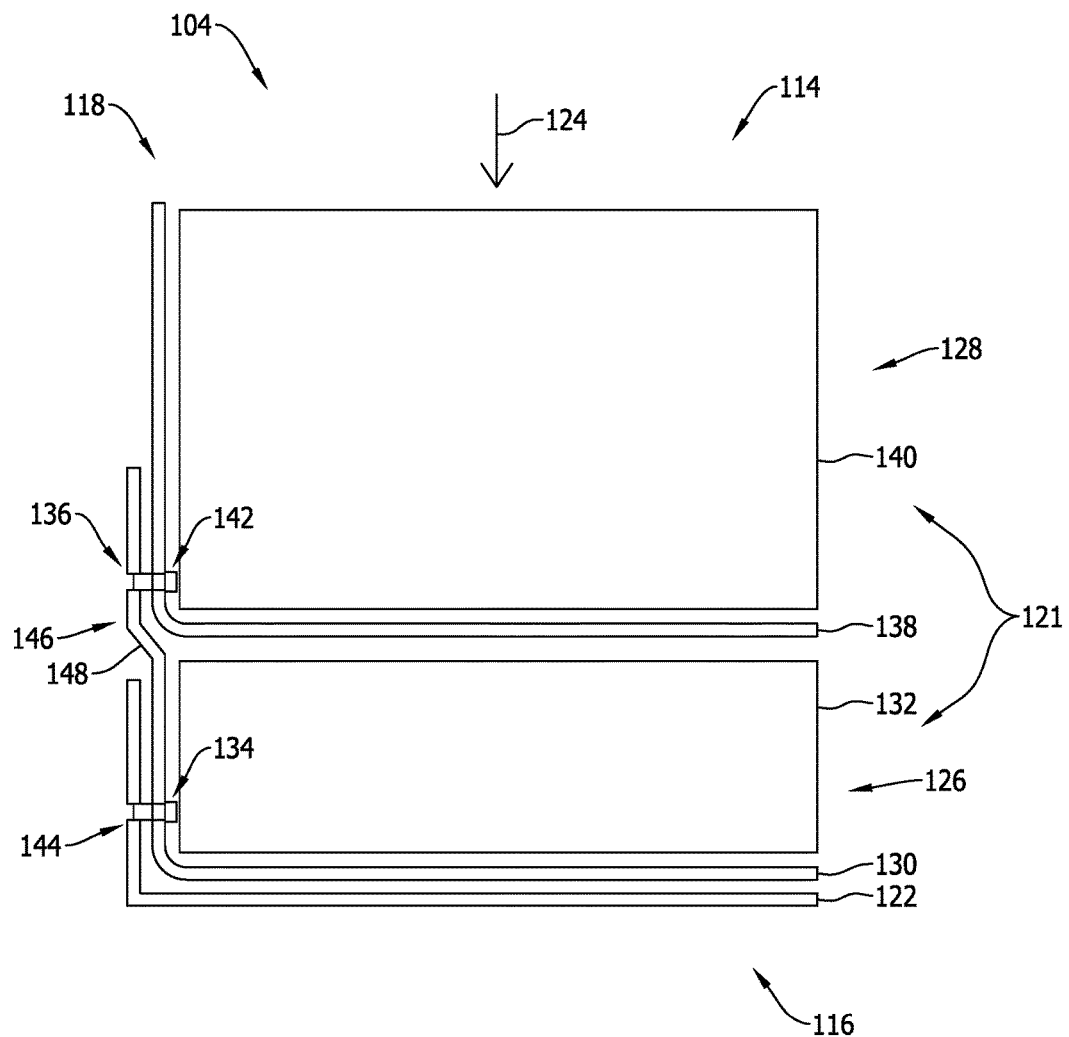
FIG. 2 is a schematic illustration of a portion of an exemplary air purification system that may be used in the air distribution system shown in FIG. 1.

FIG. 2 is a schematic illustration of a portion of an exemplary air purification system 104 that may be used in air distribution system 100 (shown in FIG. 1). In the exemplary implementation, air purification system 104 includes inlet 114, outlet 116, and filter assembly 118. Filter assembly 118 includes a plurality of filter modules 121 positioned between inlet 114 and outlet 116. Air purification system 104 also includes an intake plenum structure 122 for coupling to at least one of the plurality of filter modules 121, as will be described in more detail below. A stream 124 of air is channeled through inlet 114, through the plurality of filter modules 121, and discharged from outlet 116. In an aircraft implementation, stream 124 can be a mixed stream of ambient air and recirculated air.

Filter assembly 118 includes any number of filter modules 121 that enables air purification system 104 to function as described herein. Each filter module 121 in the plurality of filter modules 121 includes a frame, a filtration element coupled within the frame, and at least one mating feature defined in the frame, as described in more detail below. The at least one mating feature of each filter module 121 facilitates selective engagement with the at least one mating feature of another filter module 121 such that the plurality of filter modules 121 are coupled together in a serial arrangement. More specifically, the mating feature(s) of each filter module is configured to enable selective engagement of filter modules in a predetermined series. As used herein, "selective engagement" refers to the capability of a mating feature to engage with some mating features, and not with others. As such, the at least one mating feature of each filter module 121 is configured to prohibit serially coupling the plurality of filter modules 121 together in predetermined combinations based on a type of filtration element coupled within each filter module, as will be described in more detail below.

As shown in FIG. 2, filter assembly 118 includes a first filter module 126 and a second filter module 128. First filter module 126 includes a first frame 130, a first filtration element 132, a first mating feature 134, and a second mating feature 136. Second filter module 128 includes a second frame 138, a second filtration element 140, and a mating feature 142. Moreover, intake plenum structure 122 defines outlet 116, and includes a connector 144 configured for universal engagement with the at least one mating feature of each filter module 121. As such, connector 144 is engaged with first mating feature 134 of first filter module 126, and second mating feature 136 of first filter module 126 is engaged with mating feature 142 of second filter module 128 to form filter assembly 118.

In addition, in one implementation, first frame 130 of first filter module 126 includes a receiving arm 146 that extends beyond first filtration element 132 of first filter module 126. Receiving arm 146 extends beyond first filtration element 132 to provide adequate spacing between adjacent filter modules 121 when coupled together in series. More specifically, second mating feature 136 is positioned along receiving arm 146 such that second filter module 128 is coupled to first filter module 126 at receiving arm 146. Receiving arm 146 also includes a transition portion 148 oriented such that first filtration element 132 and second filtration element 140 are in alignment when first filter module 126 and second filter module 128 are coupled together. Moreover, while second filter module 128 is shown as only including one mating feature 142 and no receiving arm, it should be understood that second filter module 128 can include more than one mating feature and/or a receiving arm when designed to have subsequent filter modules 121 coupled thereto.

Figure 3:
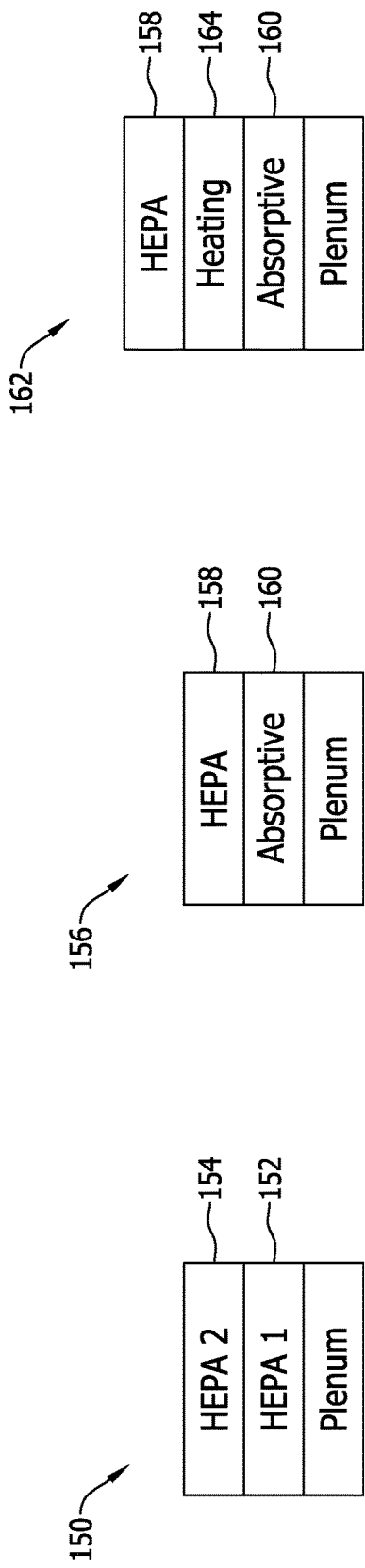
FIG. 3 is a schematic illustration of exemplary combinations of filter modules that may be used in the air purification system shown in FIG. 2.

FIG. 3 is a schematic illustration of exemplary combinations of filter modules 121 that may be used in filter assembly 118 (shown in FIG. 2). Exemplary filtration elements coupled within filter modules 121 include, but are not limited to, a particulate filter media (i.e., high-efficiency particulate air (HEPA) filter media), an absorptive filter media, and/or at least one functional filtration device, such as a regenerative heating element, an ultraviolet irradiation element, and/or an ozone converter element. The particulate filter media facilitates removing particulate contaminants from stream 124 (shown in FIG. 2), the absorptive filter media facilitates removing gaseous contaminants from stream 124, the regenerative heating element is capable of regenerating the absorptive filter media, the ultraviolet irradiation element facilitates neutralizing viruses and bacteria entrained in stream 124, and the ozone converter element is a catalytic converter device that facilitates generating oxygen from ozone-rich ambient air, for example.

As described above, the plurality of filter modules 121 in filter assembly 118 are coupled together in predetermined combinations or series based on a type of filtration element coupled within each filter module 121. More specifically, the predetermined combinations or series are determined as a function of a set of parameters, and the parameters are enforced by the mating features associated with each filter module 121, as will be described in more detail below. Moreover, in some implementations, filter modules 121 that house the same filtration element are coupled together in a single filter assembly.

In the exemplary implementation, a first parameter is that a filter module including a particulate filter media is positioned nearest inlet 114 of air purification system 104 (each shown in FIG. 2) relative to a remainder of the plurality of filter modules 121 in filter assembly 118. More specifically, the at least one mating feature of the filter module including the particulate filter media is configured based on the predetermined combinations or series such that the particulate filter module is positioned nearest inlet 114. As such, the particulate filter media removes particulate contaminants from stream 124 (shown in FIG. 2) to reduce fouling of filtration elements in downstream filter modules 121.

Moreover, when a first filter module includes a particulate filter media, and a second filter module includes an absorptive filter media, a second parameter is that the first filter module and the second filter module are coupled together such that the particulate filter media is positioned upstream from the absorptive filter media. More specifically, the at least one mating feature of the first and second filter modules are configured based on the predetermined combinations such that the particulate filter media is positioned upstream from the absorptive filter media. As such, the particulate filter media removes particulate contaminants from stream 124 to reduce fouling of the absorptive filter media.

In addition, when the second filter module includes an absorptive filter media, and a third filter module includes a regenerative heating element, a third parameter is that the regenerative heating element is positioned upstream from the absorptive filter media. More specifically, the at least one mating feature of the second and third filter modules are configured based on the predetermined combinations such that the regenerative heating element is positioned upstream from the absorptive filter media. As such, stream 124 is heated before being channeled through absorptive filter media, which facilitates regenerating the absorptive material contained within absorptive filter media.

Referring to FIG. 3, for illustrative purposes, a first predetermined combination 150 includes a first HEPA module 152 and a second HEPA module 154 coupled together in a predetermined series. In some implementations, first HEPA module 152 and second HEPA module 154 have different filtration capabilities, thereby increasing the filtration efficiency of the overall assembly.

A second predetermined combination 156 includes a HEPA module 158 and an absorptive module 160 coupled together in a predetermined series, in accordance with the first and second parameters. A third predetermined combination 162 includes HEPA module 158, a heating module 164, and absorptive module 160 coupled together in a predetermined series, in accordance with the first, second, and third parameters.

The filter assemblies shown in FIG. 3 are for example purposes only, and any filter assembly including different filtration elements, or more than one of the same filtration element, can be assembled as described herein in accordance with the parameters described above and/or other suitable parameters. In a particular embodiment, an aircraft includes any or all aspects of air purification system 104 described herein. For example, air purification system 104 is included in an ECS of the aircraft.

FIG. 4 is a schematic illustration of exemplary mating features that may be used with filter modules 121 and/or connector 144 (each shown in FIG. 2). In the exemplary implementation, different sets of mating features are shown that each include a female connector designed for female connectivity, and a male connector designed for male connectivity. More specifically, a first set 166 of mating features includes a first female mating feature 168 and a first male mating feature 170, and a second set 172 of mating features includes a second female mating feature 174 and a second male mating feature 176.

The physical design of the male and female connectors in each set of mating features determines the selective engagement between mating features in each set. For example, in the exemplary implementation, first set 166 includes a crosswise design, and second set 172 includes a vertically oriented design. As such, first female mating feature 168 is capable of engagement with first male mating feature 170 and second male mating feature 176 (i.e., first female mating feature 168 is capable of universal engagement). Conversely, first male mating feature 170 is only capable of engagement with first female mating feature 168.

Accordingly, referring to FIG. 2, the design of connector 144, first mating feature 134 and second mating feature 136 of first filter module 126, and mating feature 142 of second filter module 128 are selected to ensure first filter module 126 and second filter module 128 are coupled together in a predetermined combination based on a type of filtration element coupled within first filter module 126 and second filter module 128. In the exemplary implementation, first filter module 126 includes an absorptive filter media (e.g., filtration element 132 includes the absorptive filter media), and second filter module 128 includes a particulate filter media (e.g., filtration element 140 includes the particulate filter media). The mating features of first filter module 126 and second filter module 128 are selected in accordance with at least the parameters described above. For example, in one implementation, connector 144 is designed in accordance with first female mating feature 168. Moreover, second mating feature 136 of first filter module 126 is designed in accordance with second male mating feature 176, and mating feature 142 of second filter module 128 is designed in accordance with second female mating feature 174. As such, if filter modules housing particulate filter media are always designed in accordance with second female mating feature 174, only filter modules housing particulate filter media are capable of engagement with second mating feature 136 of first filter module 126. Alternatively, if first filter module 126 is omitted from filter assembly 118, second female mating feature 174 of second filter module 128 would also be capable of engagement with connector 144.

A method of assembling an air distribution system 100 that includes duct inlet 106 and duct outlet 110 is also described herein. The method includes positioning filter assembly 118 between duct inlet 106 and duct outlet 110, wherein filter assembly 118 includes a plurality of filter modules 121, and selectively engaging the plurality of filter modules 121 with each other such that the plurality of filter modules 121 are coupled together in a serial arrangement. In one implementation, the plurality of filter modules 121 are coupled together and then positioned between duct inlet 106 and duct outlet 110. Alternatively, filter modules 121 are individually installed between duct inlet 106 and duct outlet 110, and then coupled together. Each filter module 121 includes at least one mating feature for coupling the plurality of filter modules 121 together, and the at least one mating feature of each filter module 121 is selected such that the serial arrangement is predetermined. For example, the mating features of each filter module 121 are selected such that each filter module 121 is capable of coupling to some filter modules and not others. Positioning filter assembly 118 also includes arranging the plurality of filter modules 121 in predetermined combinations based on a type of filtration element housed within each filter module 121. For example, the predetermined combinations are also determined as a function of the type of mating feature associated with each filter module 121.

In one implementation, the plurality of filter modules 121 includes a first filter module 126 including a particulate filter media such that arranging the plurality of filter modules includes arranging first filter module 126 based on the predetermined combinations such that the particulate filter media is positioned nearest inlet 114 relative to a remainder of the plurality of filter modules 121.

In another implementation, the plurality of filter modules 121 includes a first filter module 126 including a particulate filter media, and a second filter module 128 including an absorptive filter media such that arranging the plurality of filter modules then includes arranging first filter module 126 and second filter module 128 based on the predetermined combinations such that the particulate filter media is positioned upstream from the absorptive filter media.

In yet another implementation, the plurality of filter modules 121 includes a third filter module including a regenerative heating element. Arranging the plurality of filter modules then includes arranging second filter module 128 and the third filter module based on the predetermined combinations such that the regenerative heating element is positioned upstream from the absorptive filter media.

The method further can include individually replacing each filter module 121 of the plurality of filter modules 121. As such, filter modules 121 having a shorter service life can be replaced as needed without having to replace filter modules 121 having a longer service life, or having to replace the entire filter assembly 118 from air distribution system 100.

This written description uses examples to disclose various implementations, including the best mode, and also to enable any person skilled in the art to practice the various implementations, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A filter assembly comprising:
    a plurality of filter modules, wherein each filter module in said plurality of filter modules comprises:
        a frame;
        a filtration element coupled within said frame; and
        at least one mating feature, wherein said at least one mating feature of said each filter module is configured for selective engagement with said at least one mating feature of another filter module such that said plurality of filter modules are coupled together in a serial arrangement, wherein said at least one mating feature of said each filter module is configured to prohibit serially coupling the plurality of filter modules together in predetermined combinations based on a type of filtration element coupled within said each filter module, and wherein the plurality of filter modules are selectively interchangeable with each other in different sequences to define the predetermined combinations.

2. The filter assembly in accordance with claim 1, wherein said filtration element of at least one of said filter modules comprises one of a particulate filter media and an absorptive filter media.

3. The filter assembly in accordance with claim 1, wherein said filtration element of at least one of said filter modules comprises one of a regenerative heating element, an ultraviolet irradiation element, and an ozone converter element.

4. The filter assembly in accordance with claim 1, wherein at least one filter module in said plurality of filter modules comprises a first mating feature and a second mating feature, said first mating feature configured for female connectivity, and said second mating feature configured for male connectivity.

5. The filter assembly in accordance with claim 4, wherein said frame of said at least one filter module comprises a receiving arm that extends beyond said filtration element of said at least one filter module, wherein one of said first mating feature and said second mating feature is positioned along said receiving arm.

6. An air purification system comprising:
    an inlet;
    an outlet; and
    a filter assembly comprising a plurality of filter modules positioned between said inlet and said outlet, wherein each filter module in said plurality of filter modules comprises:
        a frame;
        a filtration element coupled within said frame; and
        at least one mating feature, wherein said at least one mating feature of said each filter module is configured for selective engagement with said at least one mating feature of another filter module such that said plurality of filter modules are coupled together in a serial arrangement, wherein said at least one mating feature of said each filter module is configured to prohibit serially coupling the plurality of filter modules together in predetermined combinations based on a type of filtration element coupled within said each filter module, and wherein the plurality of filter modules are selectively interchangeable with each other in different sequences to define the predetermined combinations.

7. The system in accordance with claim 6, wherein said plurality of filter modules comprises a first filter module comprising a particulate filter media, said at least one mating feature of said first filter module configured based on the predetermined combinations such that said particulate filter media is positioned nearest said inlet relative to a remainder of said plurality of filter modules.

8. The system in accordance with claim 6, wherein said plurality of filter modules comprises a first filter module comprising a particulate filter media, and a second filter module comprising an absorptive filter media, said at least one mating feature of said first filter module and said second filter module configured based on the predetermined combinations such that said particulate filter media is positioned upstream from said absorptive filter media.

9. The system in accordance with claim 8, wherein said plurality of filter modules comprises a third filter module comprising a regenerative heating element, said at least one mating feature of said second filter module and said third filter module configured based on the predetermined combinations such that said regenerative heating element is positioned upstream from said absorptive filter media.

10. The system in accordance with claim 6 further comprising an intake plenum structure that defines said outlet, said intake plenum structure comprising a connector configured for universal engagement with said at least one mating feature of said each filter module.

11. The system in accordance with claim 6, wherein said filtration element of at least one of said filter modules comprises one of a particulate filter media and an absorptive filter media.

12. The system in accordance with claim 6, wherein said filtration element of at least one of said filter modules comprises one of a regenerative heating element, an ultraviolet irradiation element, and an ozone converter element.

13. An aircraft comprising the air purification system of claim 6.

14. A method of assembling an air purification system having an inlet and an outlet, said method comprising:
    positioning a filter assembly between the inlet and the outlet, wherein the filter assembly includes a plurality of filter modules;
    selectively engaging the plurality of filter modules with each other such that the plurality of filter modules are coupled together in a serial arrangement, wherein each filter module includes at least one mating feature for coupling the plurality of filter modules together, the at least one mating feature of said each filter module selected such that the serial arrangement is predetermined, wherein said at least one mating feature of said each filter module is configured to prohibit serially coupling the plurality of filter modules together in predetermined combinations based on a type of filtration element coupled within said each filter module; and arranging the plurality of filter modules in predetermined combinations based on the type of filtration element housed within each filter module, wherein the plurality of filter modules are selectively interchangeable with each other in different sequences to define the predetermined combinations.

15. The method in accordance with claim 14, wherein the plurality of filter modules includes a first filter module including a particulate filter media, wherein arranging the plurality of filter modules comprises arranging the first filter module based on the predetermined combinations such that the particulate filter media is positioned nearest the inlet relative to a remainder of the plurality of filter modules.

16. The method in accordance with claim 14, wherein the plurality of filter modules includes a first filter module including a particulate filter media, and a second filter module including an absorptive filter media, wherein arranging the plurality of filter modules comprises arranging first filter module and the second filter module based on the predetermined combinations such that the particulate filter media is positioned upstream from the absorptive filter media.

17. The method in accordance with claim 16, wherein the plurality of filter modules includes a third filter module including a regenerative heating element, wherein arranging the plurality of filter modules comprises arranging the second filter module and the third filter module based on the predetermined combinations such that the regenerative heating element is positioned upstream from the absorptive filter media.

18. The filter assembly in accordance with claim 1, wherein the plurality of filter modules comprise:
   a first filter module comprising a first mating feature and a second mating feature
   a second filter module comprising a third mating feature and a fourth mating feature, wherein the third mating feature is configured to engage the second mating feature, and the first mating feature and the fourth mating feature are configured to prevent engagement therebetween.

19. The filter assembly in accordance with claim 18 further comprising a third filter module comprising a fifth mating feature and a sixth mating feature, wherein the second mating feature is configured to engage either the third mating feature or the fifth mating feature, the third mating feature is configured to engage the sixth mating feature, and the first mating feature and the sixth mating feature are configured to prevent engagement therebetween.

* * * * *